US006946121B2

(12) United States Patent
Martinez et al.

(10) Patent No.: US 6,946,121 B2
(45) Date of Patent: Sep. 20, 2005

(54) COMPOSITION IN PARTICULAR COSMETIC OR DERMATOLOGICAL COMPOSITION, CONTAINING OLIGOSACCHARIDES AND PREPARATION METHOD AND COSMETIC TREATMENT METHOD

(75) Inventors: Gérard Martinez, St Clément de Rivière (FR); Christian Francisco, St Laurent de la Salanque (FR)

(73) Assignee: Laboratories G Pharm, St. Clement de Reviere (FR)

( * ) Notice: Subject to any disclaimer, the term of this patent is extended or adjusted under 35 U.S.C. 154(b) by 0 days.

(21) Appl. No.: 10/168,063

(22) PCT Filed: Dec. 20, 2000

(86) PCT No.: PCT/FR00/03607

§ 371 (c)(1),
(2), (4) Date: Jun. 19, 2002

(87) PCT Pub. No.: WO01/45713

PCT Pub. Date: Jun. 28, 2001

(65) Prior Publication Data

US 2003/0045505 A1 Mar. 6, 2003

(30) Foreign Application Priority Data

Dec. 20, 1999  (FR) ............................................. 99 16060

(51) Int. Cl.$^7$ ............................. A61K 7/06; A61K 7/00; A61K 31/715
(52) U.S. Cl. ................. 424/70.1; 424/401; 514/54
(58) Field of Search ............................. 424/70.1, 401; 514/54

(56) References Cited

U.S. PATENT DOCUMENTS 6,306,915 B1 * 10/2001 Murata ........................ 514/25

FOREIGN PATENT DOCUMENTS

EP            0 652 012 A1    5/1995

OTHER PUBLICATIONS

Patent Abstracts of Japan; JP 62 277323, Dec. 2, 1987.
Patent Abstracts of Japan; JP 11 255656, Sep. 21, 1999.
Patent Abstracts of Japan; JP 62 000412, Jan. 6, 1987.
Patent Abstracts of Japan; JP 59 176203 Oct. 5, 1984.
Patent Abstracts of Japan; JP 02 286078 Nov. 26, 1990.
Patent Abstracts of Japan; JP 57 077620 May 15, 1982.

* cited by examiner

Primary Examiner—Everett White
(74) Attorney, Agent, or Firm—Finnegan, Henderson, Farabow, Garrett & Dunner, L.L.P.

(57) ABSTRACT

The invention concerns a composition comprising at least a first constituent which is an oligosaccharide of formula (I) containing 3 to 5 oside units and having at least a D-galactose unit bound by an α[1–6] bond with a sucrose unit. The invention is characterized in that in said sucrose unit R1, R2, R3, R4, independently of one another represent a hydrogen atom, an alkyl group containing 1 to 10 carbon atoms and optionally having at least an unsaturation, a sulphate function or else an ose and, at least a second constituent which is a molecule positively charged with a physiological pH and stimulating pinocytosis or a molecule stimulating membrane penetration.

32 Claims, No Drawings

COMPOSITION IN PARTICULAR COSMETIC OR DERMATOLOGICAL COMPOSITION, CONTAINING OLIGOSACCHARIDES AND PREPARATION METHOD AND COSMETIC TREATMENT METHOD

The present invention relates to a composition, especially a cosmetic or dermatological external topical composition, containing oligosaccharides, to its preparation process and to a cosmetic treatment process comprising the application of a cosmetic composition.

The field of the present invention is that of unpleasant symptoms possibly associated with allergy and in particular with asthma, eczema, pruritus, psoriasis, allergic conjunctivitis, urticaria, reactions to insect bites, and itching, in particular symptomatic itching of major burn sufferers.

The degranulation properties of polymorphonuclear leukocytes and especially of eosinophils, basophils and mastocytes are known to be involved in allergic phenomena.

Thus, mature blood basophils have granules distributed randomly and edged with a membrane, these granules contain various products (heparin, SRS-A, ECF-A) which are released when a suitable stimulus induces a degranulation. This stimulus is usually an allergen that pairs up with the specific IgEs bound to the surface of the cell via suitable receptors. The products released by the degranulation are responsible for some of the unpleasant symptoms associated with the allergy, but they are also involved in antiparasitic immunity.

The main compounds of the prior art known for their antiallergic properties are compounds of the antihistamine family such as chloropheniramine (polaramine). These compounds are not without side effects, such as risks of drowsiness. Consequently, the present invention proposes the use of a combination of compounds that are free of the side effects of standard antihistamines and that nevertheless make it possible to treat allergies and other complaints or disorders of the same type.

The Applicant has demonstrated that the use of certain oligosaccharides is effective in reducing or even blocking the unpleasant symptoms possibly associated with allergy and as an anti-inflammatory.

Without wishing to be bound by any particular theory, it appears that the Applicant has shown that certain oligosaccharides have an antidegranulating, antigranulating or anti-activating activity on a target cell of the allergy and especially on the human basophil stimulated according to an IgE-dependent reaction.

Other specialized skin cells (such as, for example, the neurones, which, by release of substance P, are responsible for pain but also induce a degranulation of basophils) are also concerned by this activity.

The phenomenon of degranulation and also the unpleasant symptoms associated therewith are known to those skilled in the art; however, the inventors of the present patent application do not rule out the possibility that the combination used for the purposes of the present patent application intervenes upstream of the degranulation: during the maturation of the granules. Accordingly, according to the inventors, this combination might also have "antigranulating" activity.

The present invention more particularly relates to a combination comprising at least two components:
a first component that is an oligosaccharide of formula I containing from three to five saccharide units and having at least one D-galactose unit linked via an $\alpha[1-6]$ bond with a sucrose unit:

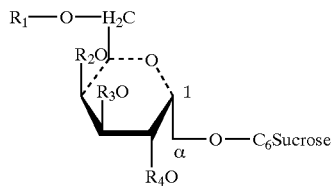

Formula I in which $R_1$, $R_2$, $R_3$ and $R_4$, independently of each other, represent a hydrogen atom, an alkyl group containing from 1 to 10 carbon atoms and optionally having at least one unsaturation, an acid function containing from 1 to 10 carbon atoms and optionally having at least one unsaturation, a sulfate function or a monosaccharide,
and at least one second component that is a molecule that is positively charged at physiological pH and that promotes pinocytosis and/or a molecule that promotes membrane penetration.

The second component acts as a vector for the first component, this first component being the active principle. The essential role of this second component is to allow the first component, the active principle, to cross the white blood cell membrane.

Said oligosaccharide may be chosen in particular from the group consisting of raffinose and stachyose in free or derived form. The second component is preferably a saponin or a basic amino acid, and it is chosen even more preferably from the group consisting of saponins and arginine.

Preferably, the following natural saponins will be used: harpagosides, ginsenosides, saponins of quillaja saponaria QS III and QS 21A type.

The present invention relates to the use of a combination of at least two components for the manufacture of a cosmetic composition for inhibiting the granulation and/or degranulation of white blood cells, which is intended to be administered topically and externally or by inhalation, such that the first component—the active principle—is an oligosaccharide of formula I containing from three to five saccharide units and having at least one D-galactose unit linked via an $\alpha[1-6]$ bond to a sucrose unit:

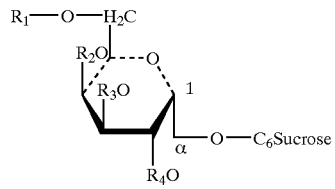

in which $R_1$, $R_2$, $R_3$ and $R_4$, independently of each other, represent a hydrogen atom, an alkyl group containing from 1 to 10 carbon atoms and optionally having at least one unsaturation, an acid function containing from 1 to 10 carbon atoms and optionally having at least one unsaturation, a sulfate function or a monosaccharide, said oligosaccharide preferably being chosen from the group consisting of raffinose and stachyose in free or derived form, and
the second component, which is a molecule that is positively charged at physiological pH and that promotes pinocytosis and/or a molecule that promotes membrane penetration.

Said cosmetic composition may also contain an antiallergic component.

The preferred combinations for use for the purposes of the present invention are the following: the oligosaccharide is raffinose in free or derived form and the second component a saponin; the oligosaccharide is raffinose in free or derived form and the second component is arginine; the oligosaccharide is stachyose in free or derived form and the second component is a saponin; the oligosaccharide is stachyose in free or derived form and the second component is arginine.

According to one preferred form, said composition is such that the weight concentration of oligosaccharide is between 0.01% and 20% relative to the total mass of the composition and preferably between 0.01% and 10% relative to the total mass of the composition. Preferably, the concentration of the second component (saponins and arginine) is preferably between 5% and 20% by weight relative to the oligosaccharide concentration and preferably about 10% by weight relative to the oligosaccharide concentration.

This composition also generally contains at least one cosmetically acceptable excipient.

The cosmetic compositions used according to the present invention may be in the form of a solution, an emulsion, a cream, an ointment, a powder, a milk, a lotion, a gel or a paste with water. Without wishing to be bound by any particular theory, it would appear that ingestion (drinks, lozenges or gel capsules) makes the composition ineffective since, quite probably, the enzymatic systems of the stomach destroy the sucrose part of the molecule, converting it into melibiose. However, in vitro studies showed that melibiose was not active on leukocytes.

A subject of the present invention is also a cosmetic treatment process such that said cosmetic composition is applied topically.

A subject of the present invention is also the use of a combination of at least two components for the manufacture of a dermatological composition, i.e. a composition as a medicinal product, to inhibit the granulation and/or degranulation of white blood cells, which is intended to be used externally and topically or by inhalation. This composition is especially intended for treating at least one symptom possibly associated with allergy, chosen from the group consisting of asthma, eczema, pruritus, psoriasis, allergic conjunctivitis, urticaria, reactions to insect bites, and itching, in particular symptomatic itching of major burn sufferers, or as an anti-inflammatory, in particular for treating arthrosis.

The present invention relates to the use, for the manufacture of a medicinal product for inhibiting the granulation and/or degranulation of white blood cells, which is intended to be taken in the form of ointments, creams, eyedrops, aerosols (sprays), lotions or by inhalation, of a composition comprising at least:

the first component—the active principle—of said combination is an oligosaccharide of formula I containing from three to five saccharide units and having at least one D-galactose unit linked via an α[1–6] bond to a sucrose unit:

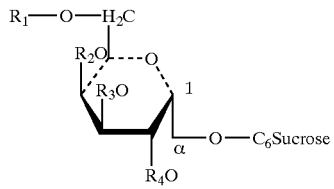

in which $R_1$, $R_2$, $R_3$ and $R_4$, independently of each other, represent a hydrogen atom, an alkyl group containing from 1 to 10 carbon atoms and optionally having at least one unsaturation, an acid function containing from 1 to 10 carbon atoms and optionally having at least one unsaturation, a sulfate function or a monosaccharide, said oligosaccharide preferably being chosen from the group consisting of raffinose and stachyose in free or derived form, and the second component is a molecule that is positively charged at physiological pH and that promotes pinocytosis, or a molecule that promotes membrane penetration, this second component preferably being chosen from the group consisting of saponins and arginine.

The combinations that are preferred for use for the purposes of the present invention are as follows: the oligosaccharide is raffinose in free or derived form and the second component is a saponin; the oligosaccharide is raffinose in free or derived form and the second component is arginine; the oligosaccharide is stachyose in free or derived form and the second component is a saponin; the oligosaccharide is stachyose in free or derived form and the second component is arginine.

According to one preferred form, said composition is such that the weight concentration of oligosaccharide is between 0.01% and 20% relative to the total mass of the composition and preferably between 0.01% and 10% relative to the total mass of the composition. Preferably, the concentration of the second component (saponins, arginine) is preferably between 5% and 20% by weight relative to the oligosaccharide concentration and preferably about 10% by weight relative to the oligosaccharide concentration.

Said composition as a medicinal product may also contain an antiallergic component.

Said medicinal product advantageously contains at least one pharmaceutically acceptable excipient.

This medicinal product may be intended for local or general treatment and may be in the form of a solution, an emulsion, a cream, an ointment, a powder, a milk, a lotion, a gel or paste with water, eyedrops or a spray.

The main indications of this medicinal product are the treatments of at least one symptom possibly associated with an allergy chosen from the group consisting of asthma, eczema, pruritus, psoriasis, allergic conjunctivitis, urticaria, reactions to insect bites, or itching, in particular symptomatic itching of major burn sufferers, and this medicinal product is also recommended as an anti-inflammatory, in particular for treating arthrosis.

A subject of the present invention is also a process for preparing a composition according to the invention such that at least the following are mixed together:

an oligosaccharide of formula I, optionally at least one second component, which is a molecule that is positively charged at physiological pH and that promotes pinocytosis, or a molecule that promotes membrane penetration, optionally an antiallergic component.

These oligosaccharides consisting of galactose units linked via one (or more) bonds of α type between them and to a sucrose unit, are the storage substances of a certain number of plants (bean, pea, soybean, etc.) and are especially known for their responsibility for the phenomenon of flatulence in man. On the other hand, no direct action of possible therapeutic (dermatological) or cosmetic interest has ever been demonstrated to date.

Without wishing to be bound by any particular theory, these molecules were tested on the antidegranulating activity of human basophils, starting from the idea that since mammalian bodies do not have the enzymes necessary to degrade α-linked galactose units, these oligosaccharides might disrupt the glycolysis of mastocytes, i.e. the energy source for granulation and degranulation.

The oligosaccharides used to carry out the present invention comprise from three to five saccharide units, with at least one D-galactose unit linked via its carbon 1 to carbon 6 of a sucrose unit, via an α bond according to formula I below:

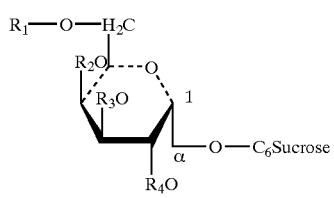

in which $R_1$, $R_2$, $R_3$ and $R_4$ represent, independently of each other, a hydrogen atom, an alkyl group containing from 1 to 10 carbon atoms and optionally having at least one unsaturation, an acid function containing from 1 to 10 carbon atoms and optionally having at least one unsaturation, a sulfate function or a monosaccharide, which may be in free or derived form.

In addition, the sucrose unit may also be in free form (that is to say a sugar in which the alcohol functions are unprotected) or derived form. Moreover, this sucrose unit appears to be essential for the biological activity since melibiose, tested under the same experimental conditions, shows absolutely no activity on mastocytes.

For the purposes of the present invention, the expression "derived form" means that the alcohol functions are substituted, for example, with an acetyl group ($CH_3CO$), etc.

Preferably, stachyose and raffinose will be used.

Stachyose is a tetraholoside whose final structure is:

α-D-galactopyranosyl-(1–6)-α-D-galactopyranosyl-(1–6)-α-D-glucopyranosyl-(1–2)-β-D-fructofuranoside.

Stachyose and raffinose correspond to the formula given below.

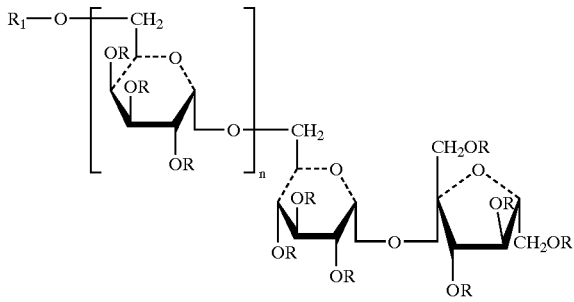

in which, for stachyose, R=H and n=2 and, for raffinose, R=H and n=1.

The compositions, in particular the cosmetic compositions or compositions as medicinal (dermatological) product, according to the invention may be in the form of ointments, creams, eyedrops, sprays or lotions for local administration, in combination with compatible excipients. The excipients generally used to prepare such compositions are binders, preserving agents, flavorings, etc. In these forms, the weight percentage of active principle relative to the mass of the total composition is between 0.01% and 20% and preferably 0.2% and 1%. Pharmaceutical compositions for inhalation may also be prepared for internal treatments (asthma).

In order to test the antidegranulating or antiactivating activity of the oligosaccharides on human basophils by flow cytometry, leukocyte suspensions from different individuals selected as being good at responding to anti-IgE were used to isolate the leukocytes, by simple sedimentation at 1 g. These leukocytes are preincubated for 30 minutes with successive dilutions from 10 to 0.01 mg/ml of the test product. The basophils are then stimulated with a target concentration of a human anti-IgE labeled with a mixture of anti-IgE FITC and anti-CD63PE antibodies, CD63 being an activation label for human basophils. The percentages of activation or of inhibition are then calculated by flow cytometry. The biological activity of the oligosaccharides was thus evaluated.

The chemical structure of the commercial molecules and derivatives, in particular that of stachyose, was confirmed by NMR: $^1H$ and $^{13}C$ NMR, 2D-NMR (DQF-cosy, HMQC and HMBC).

The same biological tests were performed on structural analogs such as raffinose or oligosaccharides comprising an α bond between a galactose unit and another saccharide unit such as in melibiose.

These highly water-soluble molecules have little chance of crossing the liposoluble membranes of the mastocytes, as confirmed by the test results.

However, it is well known that the mastocytes show large pinocytotic activity with respect to molecules that are positively charged (i.e. bases) at physiological pH.

Tests were thus undertaken. The aim of these tests is to test the degranulation-inhibiting power of compositions containing a first component—the active principle—which is an oligosaccharide chosen from stachyose and raffinose at different concentrations and a second component chosen from the group supplied by arginine, choline, calcium chloride ($CaCl_2$) and saponin. The percentage of inhibition was calculated by repeating the experiment three times.

The results obtained are given in table 1, and the following abbreviations have been used:

| "S": for stachyose | "R": for raffinose |
| "10": for 10 mg/ml | "1": for 1 mg/ml |
| "0.1": for 0.1 mg/ml | "a": for arginine |
| "b": for choline | "c": for $CaCl_2$ |
| "Sp": for saponin | "NT": for not tested. |

| Composition | $S_{10}a$ | $S_1a$ | $S_{0.1}a$ | $S_{10}b$ | $S_1b$ | $S_{0.1}b$ |
|---|---|---|---|---|---|---|
| % of inhibition | 31 | 15 | 0 | 9 | 0 | 0 |
| Composition | $S_{10}c$ | $S_1c$ | $S_{0.1}c$ | $S_{10}sp$ | $S_1sp$ | $S_{0.1}sp$ |
| % of inhibition | 6 | 0 | 0 | 76 | 0 | 0 |
| Composition | $R_{10}a$ | $R_1a$ | $R_{0.1}a$ | $R_{10}b$ | $R_1b$ | $R_{0.1}b$ |
| % of inhibition | 19 | 5 | 0 | 2 | NT | NT |
| Composition | $R_{10}c$ | $R_1c$ | $R_{0.1}c$ | $R_{10}sp$ | $R_1sp$ | $R_{0.1}sp$ |
| % of inhibition | 0 | NT | NT | 77 | 10 | 0 |

In the light of these results, it is clearly seen that, at the concentrations tested, the compositions containing arginine and stachyose or raffinose make it possible to inhibit the degranulation or the initiation of the granulation system and thus to inhibit the release of histamine, bradykinin, serotonin and the chemotactic factors of other leukocytes.

In order to obtain a greater inhibition of mastocytes we then undertook to promote the penetration of these molecules across the membranes by replacing the arginine with saponin (Quillaja bark). The results of table 1 show that even higher percentages of inhibition are then obtained.

The use of the oligosaccharides according to the present invention, in the presence of molecules that are positively charged at physiological pH (for example such as arginine) and promote pinocytosis, or of molecules that promote membrane penetration (for example saponins) thus make it possible to block or reduce the biological activities of the mastocytes, basophils and eosinophils in mammals.

No cytotoxic activity was observed during the biological studies. Molecules of this type may thus be used beneficially in all the therapeutic (dermal) and cosmetic fields in which human mastocytes and basophils (and consequently eosinophils) are involved. Examples that are mentioned include pruritus, insect bites, psoriasis, allergic conjunctivitis, urticaria, eczema and asthma.

The examples that follow do not in any way limit the scope of the present invention.

| Formulation Examples | |
|---|---|
| Topical gel | |
| Oligosaccharide | 0.1 g |
| Arginine (or saponins) | 0.01 g |
| Methylcellulose | 3 g |
| Purified water qs | 100 g |
| Preserving agents, fragrance | qs |
| Fatty cream | |
| Oligosaccharide | 0.1 g |
| Arginine (or saponins) | 0.01 g |
| Purified water | 5 ml |
| Preserving agents, fragrance (applied in unmodified form or as a greasy tulle) | qs |
| Emulsion | |
| Oligosaccharide | 0.2 g |
| Arginine (or saponins) | 0.02 g |
| PEG-1500 monostearate | 5 g |
| PEG-300 monostearate | 2 g |
| Fluid liquid paraffin | 5 g |
| Purified water qs | 100 g |
| Preserving agents, fragrance | qs |
| Inhalation | |
| A preparation for inhalation is obtained from the following mixture: | |
| Oligosaccharide | 100 mg |
| Arginine (or saponins) | 10 mg |
| Excipient | 10 g |

A standard excipient for an inhalation formulation, for example such as oleic acid, and a propellent gas such as trichlorofluoromethane or dichlorodifluoromethane, are added to this mixture.

Greasy Cream A (% formulation)

| Components | % |
|---|---|
| Water | 54.60 |
| PEG-6 and PEG-32 stearate | 12.00 |
| *Butyrospermum parkii* | 10.00 |
| Raffinose | 10.00 |
| Glycerol | 7.00 |
| Liquid paraffin | 3.00 |
| Stearic acid | 1.20 |
| Saponin | 1.00 |
| Methylparaben | 0.20 |
| Imidazolidinyl urea | 0.20 |
| Bisabolol | 0.20 |
| Fragrance | 0.20 |
| Propylparaben | 0.10 |
| BHT, BHA, propyl gallate and citric acid | 0.05 |
| Benzyl alcohol, methyl-chloroisothiazolinone and methylisothiazolinone | 0.05 |

Antipruriginous Effect on the Recently Epidermized Tegument of a Major Burn Sufferer During the cicatrization phase, major burn sufferers experience intense itching, even occasionally under heavy antihistamine treatment.

This study, which lasted one year, performed on 33 patients, demonstrated the powerful antipruriginous effect of composition A in this indication.

Protocol

Patients suffering from itching are treated with an application of composition A whose raffinose concentration is 10%, or with an application of composition A' whose raffinose concentration is 5%, or alternatively with an application of composition A" whose raffinose concentration is 3%, the application being attributed at random. The percentage of saponin in compositions A' and A" represents one tenth of the raffinose concentration.

In the event of a second area to be treated in parallel, the patient is treated under double blind conditions and without his knowledge with a composition considered as a placebo on this second area, containing the same excipients but not containing any raffinose or saponin.

The three tubes with different concentrations of raffinose are coded for the patient and the staff responsible for applying them.

The applications are repeated several times a day in the event of itching and at the request of the patient and may be spread over several days.

A monitoring sheet indicates the time of action of the product(s) according to an analog scale of the pruritus from 0 to 10.

Results and Conclusions

Out of 33 cases treated, 30 showed an action of the product, and 3 were found to be negative.

8 cases involved two areas of application against placebo.

The average time of action of composition A in the 30 positive cases is between 2 and 5 minutes, with an average duration of action of between 3 and 4 hours.

The intensity of the initial pruritus estimated on average as 7 on the analog scale, is 0 in the 30 cases after 15 minutes.

No statistically significant difference could be demonstrated as regards the three doses of raffinose.

Against placebo, the same effects as above are still observed for the area treated with composition A.

For the area treated with the placebo, the intensity of the pruritus decreases slightly from 0 to 5 minutes and then returns to the initial level of intensity after 5 to 15 minutes. This well-known transient phenomenon is linked to the moisturization of the skin.

No intolerance phenomena were reported during the study in single or repeated application.

It should be noted that one case of eczema regressed under the effect of the treatment.

Out of 3 negative cases, one is unexplained and, as for the other two patients, one suffered from a very intense inflammation and the other from a burning sensation, but not really pruritus.

What is claimed is:

1. A method for inhibiting the granulation and/or degranulation of white blood cells in a patient, comprising the topical external administration of a composition, wherein the composition comprises:
an oligosaccharide of formula I, which is the active principle, containing from three to five saccharide units and having at least one D-galactose unit linked via an α[1–6] bond with a sucrose unit:

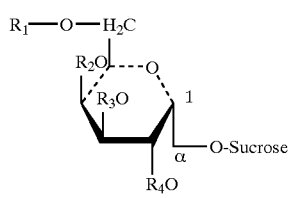

in which $R_1$, $R_2$, $R_3$ and $R_4$ represent, independently of each other, a hydrogen atom, an alkyl group containing from 1 to 10 carbon atoms and optionally having at least one unsaturation, an acid function containing from 1 to 10 carbon atoms and optionally having at least one unsaturation, and a sulfate function or a monosaccharide; and a molecule that is positively charged at physiological pH and promotes pinocytosis, or a molecule that promotes membrane penetration;

wherein the composition is administered in an amount sufficient to inhibit the granulation and/or degranulation of white blood cells in the patient.

2. The method of claim 1, wherein the oligosaccharide is raffinose.

3. The method of claim 1 or 2, wherein the molecule that is positively charged at physiological pH and promotes pinocytosis, or that promotes membrane penetration, is a saponin or is arginine.

4. The method of claim 1, wherein the oligosaccharide is raffinose and the molecule that is positively charged at physiological pH and promotes pinocytosis, or that promotes membrane penetration, is a saponin.

5. The method of claim 1, wherein the oligosaccharide is raffinose and the molecule that is positively charged at physiological pH and promotes pinocytosis, or that promotes membrane penetration, is arginine.

6. The method of claim 1, wherein the oligosaccharide is stachyose and the molecule that is positively charged at physiological pH and promotes pinocytosis, or that promotes membrane penetration, is a saponin.

7. The method of claim 1, wherein the oligosaccharide is stachyose and the molecule that is positively charged at physiological pH and promotes pinocytosis, or that promotes membrane penetration, is arginine.

8. The method of claim 1, wherein the weight concentration of oligosaccharides in the composition is between 0.01% and 20% relative to the total mass of the composition.

9. The method of claim 1, wherein the concentration of the molecule that is positively charged at physiological pH and promotes pinocytosis, or that promotes membrane penetration, in the composition is between 5% and 20% by weight relative to the oligosaccharide concentration.

10. The method of claim 1, wherein the composition further comprises an antiallergic component.

11. The method of claim 1, wherein the weight concentration of oligosaccharides in the composition is between 0.01% and 10% relative to the total mass of the composition and the concentration of the molecule that is positively charged at physiological pH and promotes pinocytosis, or that promotes membrane penetration, in the composition is about 10% by weight relative to the oligosaccharide concentration.

12. The method of claim 1, for the treatment of at least one symptom associated with an allergy chosen from the group consisting of eczema, pruritus, psoriasis, allergic conjunctivitis, urticaria, reactions to insect bites, and itching, or as an anti-inflammatory.

13. The method of claim 12, for the treatment of the symptomatic itching of major burn sufferers or for the treatment of arthrosis.

14. The method of claim 1, wherein the composition is administered to the patient in the form of an ointment, a cream, eyedrops, a lotion, or a spray intended for external use.

15. The method of claim 1, wherein the composition to be administered is a cosmetic or dermatological composition.

16. The method of claim 1, wherein the composition further comprises at least on acceptable excipient.

17. A method for treating an allergy and/or inflammatory condition in a patient by inhibiting the granulation and/or degranulation of white blood cells in the patient, the method comprising administering a composition to the patient by topical external administration, wherein the composition comprises:

an oligosaccharide of formula I, containing from three to five saccharide units and having at least one D-galactose unit linked via an α[1–6] bond with a sucrose unit:

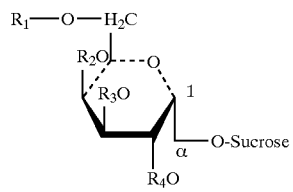

in which $R_1$, $R_2$, $R_3$ and $R_4$ represent, independently of each other, a hydrogen atom, an alkyl group containing from 1 to 10 carbon atoms and optionally having at least one unsaturation, an acid function containing from 1 to 10 carbon atoms and optionally having at least one unsaturation, and a sulfate function or a monosaccharide; and a molecule that is positively charged at physiological pH and promotes pinocytosis, or a molecule that promotes membrane penetration;

wherein the composition is administered in an amount sufficient to treat an allergy and/or inflammatory condition in the patient by inhibiting the granulation and/or degranulation of white blood cells in the patient.

18. A method for inhibiting the granulation and/or degranulation of white blood cells in a patient, comprising the administration by inhalation of a composition, wherein the composition comprises:

an oligosaccharide of formula I, which is the active principle, containing from three to five saccharide units and having at least one D-galactose unit linked via an α[1–6] bond with a sucrose unit:

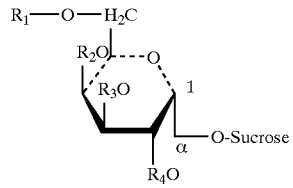

in which $R_1$, $R_2$, $R_3$ and $R_4$ represent, independently of each other, a hydrogen atom, an alkyl group containing from 1 to 10 carbon atoms and optionally having at least one unsaturation, an acid function containing from 1 to 10 carbon atoms and optionally having at least one unsaturation, and a sulfate function or a monosaccharide; and a molecule that is positively charged at physiological pH and promotes pinocytosis, or a molecule that promotes membrane penetration;

wherein the composition is administered in an amount sufficient to inhibit the granulation and/or degranulation of white blood cells in the patient.

19. The method of claim 18, wherein the oligosaccharide is raffinose or stachyose.

20. The method of claim 18 or 19, wherein the molecule that is positively charged at physiological pH and promotes pinocytosis, or that promotes membrane penetration, is a saponin or is arginine.

21. The method of claim 18, wherein the oligosaccharide is raffinose and the molecule that is positively charged at physiological pH and promotes pinocytosis, or that promotes membrane penetration, is a saponin.

22. The method of claim 18, wherein the oligosaccharide is raffinose and the molecule that is positively charged at physiological pH and promotes pinocytosis, or that promotes membrane penetration, is arginine.

23. The method of claim 18, wherein the oligosaccharide is stachyose and the molecule that is positively charged at physiological pH and promotes pinocytosis, or that promotes membrane penetration, is a saponin.

24. The method of claim 18, wherein the oligosaccharide is stachyose and the molecule that is positively charged at physiological pH and promotes pinocytosis, or that promotes membrane penetration, is arginine.

25. The method of claim 18, wherein the weight concentration of oligosaccharides in the composition is between 0.01% and 20% relative to the total mass of the composition.

26. The method of claim 18, wherein the concentration of the molecule that is positively charged at physiological pH and promotes pinocytosis, or that promotes membrane penetration, in the composition is between 5% and 20% by weight relative to the oligosaccharide concentration.

27. The method of claim 18, wherein the composition further comprises an antiallergic component.

28. The method of claim 18, wherein the weight concentration of oligosaccharides in the composition is between 0.01% and 10% relative to the total mass of the composition and the concentration of the molecule that is positively charged at physiological pH and promotes pinocytosis, or that promotes membrane penetration, in the composition is about 10% by weight relative to the oligosaccharide concentration.

29. The method of claim 18, for the treatment of at least one symptom associated with asthma, or as an anti-inflammatory.

30. The method of claim 18, wherein the composition is administered to the patient in the form of a spray for inhalation.

31. The method of claim 18, wherein the composition further comprises at least on acceptable excipient.

32. A method for treating an allergy and/or inflammatory condition in a patient by inhibiting the granulation and/or degranulation of white blood cells in the patient, the method comprising administering a composition to the patient by inhalation, wherein the composition comprises:

an oligosaccharide of formula I, containing from three to five saccharide units and having at least one D-galactose unit linked via an α[1–6] bond with a sucrose unit:

in which $R_1$, $R_2$, $R_3$ and $R_4$ represent, independently of each other, a hydrogen atom, an alkyl group containing from 1 to 10 carbon atoms and optionally having at least one unsaturation, an acid function containing from 1 to 10 carbon atoms and optionally having at least one unsaturation, and a sulfate function or a monosaccharide; and a molecule that is positively charged at physiological pH and promotes pinocytosis, or a molecule that promotes membrane penetration;

wherein the composition is administered in an amount sufficient to treat an allergy and/or inflammatory condition in the patient by inhibiting the granulation and/or degranulation of white blood cells in the patient.

* * * * *

UNITED STATES PATENT AND TRADEMARK OFFICE
CERTIFICATE OF CORRECTION

PATENT NO. : 6,946,121 B2
APPLICATION NO. : 10/168063
DATED : September 20, 2005
INVENTOR(S) : Gérard Martinez et al.

It is certified that error appears in the above-identified patent and that said Letters Patent is hereby corrected as shown below:

Title page,
Item [54] Title, "COMPOSITION IN" should read -- COMPOSITION, IN --.
Item [73], Assignee, "Reviere" should read -- Rivière --.
Item [57], ABSTRACT,
Line 3, "oside" should read -- saccharide --.

Column 7,
Line 34, "Inhalation" should read -- Inhalation --.

Column 9,
Line 24, "raffinose" should read -- raffinose or stachyose --.

Column 10,
Line 8, "on" should read -- one --.

Column 12,
Line 8, "on" should read -- one --.

Signed and Sealed this

Twenty-seventh Day of June, 2006

JON W. DUDAS
*Director of the United States Patent and Trademark Office*